United States Patent
Long et al.

(10) Patent No.: US 8,467,588 B2
(45) Date of Patent: Jun. 18, 2013

(54) VOLUME-OF-INTEREST SEGMENTATION SYSTEM FOR USE WITH MOLECULAR IMAGING QUANTIZATION

(75) Inventors: An-Jim Long, Taoyuan County (TW); Chih-Hsien Chang, Hsinchu (TW); Te-Wei Lee, Taipei (TW)

(73) Assignee: Institute of Nuclear Energy Research Atomic Energy Council, Taoyuan (TW)

( * ) Notice: Subject to any disclaimer, the term of this patent is extended or adjusted under 35 U.S.C. 154(b) by 66 days.

(21) Appl. No.: 13/283,762

(22) Filed: Oct. 28, 2011

(65) Prior Publication Data

US 2012/0134544 A1 May 31, 2012

(30) Foreign Application Priority Data

Nov. 29, 2010 (TW) ................................ 99141209 A

(51) Int. Cl.
*G06K 9/00* (2006.01)

(52) U.S. Cl.
USPC ........... 382/131; 382/110; 382/173; 382/256; 382/128; 382/133

(58) Field of Classification Search
None
See application file for complete search history.

(56) References Cited

U.S. PATENT DOCUMENTS

| | | | |
|---|---|---|---|
| 5,881,124 A * | 3/1999 | Giger et al. ................... | 378/8 |
| 6,556,696 B1 * | 4/2003 | Summers et al. ............. | 382/128 |
| 6,853,741 B1 * | 2/2005 | Ruth et al. .................... | 382/132 |
| 6,993,174 B2 * | 1/2006 | Fan et al. ...................... | 382/131 |
| 7,548,649 B2 * | 6/2009 | Cardenas et al. ............. | 382/173 |
| 7,586,490 B2 * | 9/2009 | McDaniel ...................... | 345/441 |
| 7,660,451 B2 * | 2/2010 | Reeves et al. ................. | 382/131 |
| 7,831,079 B2 * | 11/2010 | Kunz et al. .................... | 382/128 |
| 8,145,292 B2 * | 3/2012 | Vining .......................... | 600/407 |
| 8,155,405 B2 * | 4/2012 | Unal et al. ..................... | 382/128 |
| 8,199,981 B2 * | 6/2012 | Koptenko et al. ............. | 382/128 |
| 8,301,228 B2 * | 10/2012 | Kindlein et al. .............. | 600/436 |
| 2002/0156361 A1 * | 10/2002 | Popowski et al. ............. | 600/407 |
| 2003/0048936 A1 * | 3/2003 | Fan et al. ...................... | 382/131 |
| 2008/0025584 A1 * | 1/2008 | Kunz et al. .................... | 382/128 |
| 2009/0136103 A1 * | 5/2009 | Sonka et al. .................. | 382/128 |
| 2010/0080354 A1 * | 4/2010 | Fu et al. ........................ | 378/65 |
| 2010/0266170 A1 * | 10/2010 | Khamene et al. ............. | 382/128 |
| 2010/0322493 A1 * | 12/2010 | Wei et al. ...................... | 382/128 |
| 2011/0044523 A1 * | 2/2011 | Gloger .......................... | 382/131 |
| 2013/0004043 A1 * | 1/2013 | Ross et al. .................... | 382/131 |

OTHER PUBLICATIONS

WO011339, Dean, H, David., Mand Apparatus for producing an implantm 2001.*

* cited by examiner

*Primary Examiner* — Jayesh A Patel
*Assistant Examiner* — Iman K Kholdebarin
(74) *Attorney, Agent, or Firm* — WPAT, PC; Justin King

(57) ABSTRACT

The present invention relates to a volume-of-interest segmentation system for use with molecular imaging quantization, which includes: a set of template for segmentation of organ/anatomical region-of-interest, an animal size/weight/location calculator, an animal spine position calculator, and a texture analyzer. It can be used for saving time and reducing cost for segmentation of interested regions and increasing the precision of molecular image quantization.

5 Claims, 7 Drawing Sheets

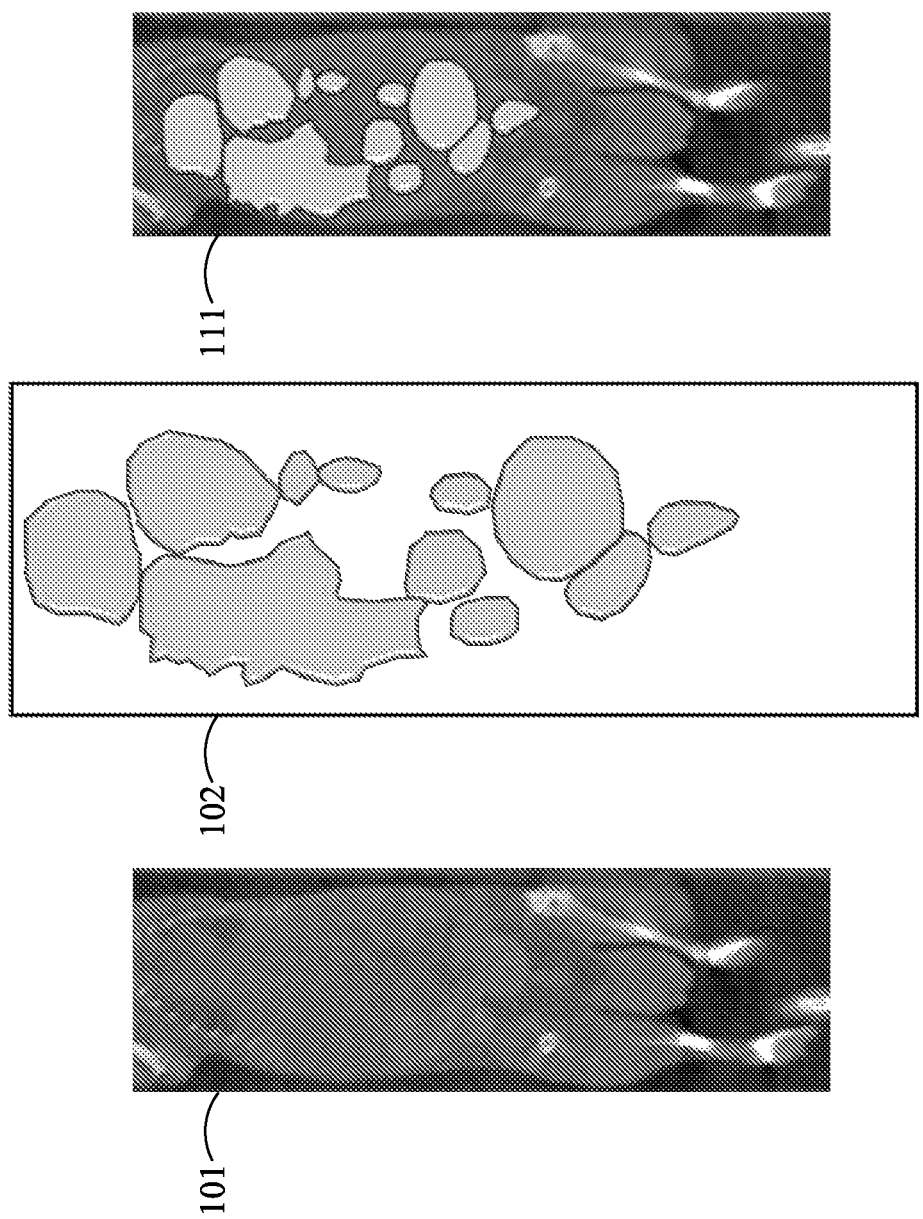

VOLUME-OF-INTEREST SEGMENTATION SYSTEM FOR USE WITH MOLECULAR IMAGING QUANTIZATION

TECHNICAL FIELD

The invention relates to a Volume-of-interest (VOI) segmentation system for use with molecular imaging quantization, more particularly to the method and system utilized in vivo quantization of nuclear medicine and clinical imaging modalities.

TECHNICAL BACKGROUND

As is known in the art, molecular imaging refers to a multi-discipline at the intersection of molecular biology and in vivo imaging. This provides molecular level of information in a noninvasive manner. Preclinical research and development is no doubt the most critical application of molecular imaging. Highly available live information from molecular imaging for observation of functional activity between organs is very helpful for screening and investigation of new drugs.

There are many different image modalities of molecular imaging. Among the modalities, Computed Tomography (CT), Positron Emission Tomography (PET), Single Photon Emission Computed Tomography (SPECT), In Vivo Bioluminescence System and Magnetic Resonance Imaging (MRI) are with the best image resolution and are among the most important modalities. Normally these modalities are with high sensitivity and provide micron level of resolution especially nuclear medicine modalities such as PET and SPECT by using trace level radiopharmaceuticals. Quantization of molecular imaging information is then becoming an important issue since these radiopharmaceuticals are not only going to be used in animals, but also to the human. Pharmacokinetic, bio-distribution, and radiation dosimetry can then be obtained without sacrificing animals or invasive surgery to the human.

To better quantization of images generated by molecular imaging modalities, precise three dimension (3D) segmentation of the target is required to be provided. Taking SPECT/CT image quantization as an example, quantization of a specified segmentation from SPECT planar can vary from −14%~50%, quantization of SPECT can vary from −40%~52%, while SPECT/CT can vary from −22%~24%. Although the above results are statistically meaningful for scientific research, the results are still worse than imaging of phantom and its quantization. The major reason is how region-of-interest (ROI) or VOI is defined especially its size and location. In the conventional method, sphere and cube for VOI, circle and square for ROI, and segmentation defined by free hand are provided to localize the target. Some commercial software provides automatic VOI/ROI selection by definition of threshold. However, threshold selection is based on contrast of the image (normally presented by color of each channel such as red, green, and blue) and can be confounded by noisy signals or signals coming from conjunction organs therefore the variation can be enlarged. Freehand definition of VOI/ROI made by professional molecular imaging experts always gets the best quality of quantization. However, better resolution means more efforts to define ROI of the target areas and more ROIs to a VOI. It makes 3D segmentation the most time consuming job during image quantization.

TECHNICAL SUMMARY

In accordance with the present invention, a system is provided for enhancement of segmentation for molecular imaging quantization. This System comprises: an organ/anatomic segmentation template, which contains one or more 3D VOI segmentation areas and parameters for adjustment of size, shape and location of the segmentation group; an animal size and weight calculator, to be used for input of animal size and weight and converts into parameters for adjustment of size, shape and location of the segmentation template; an animal spine position calculator, which is used to define animal bone skeleton and identify spine direction and detailed position by longest bone pathway for conversion of parameters for adjustment of size and shape of the segmentation template; and a texture analyzer, which is used to define a series of segmentations with similar texture for further match of template and the image for adjustment of size, shape and location of the segmentation template.

In one embodiment, A VOI Segmentation System for use with Molecular Imaging Quantization comprising the steps of: (a) preparation for and of the image, which includes preparation of animal, imaging of the animal, fusion of different modalities, and contract adjustment for the image; (b) importing the said fusion image into said VOI Segmentation System comprising an organ/anatomic segmentation template, an animal size and weight calculator, an animal spine position calculator, and a texture analyzer; (c) selection of predefined segmentation template based on study target, animal species, organ and anatomic target of interests; (d) identifying animal width, height, depth, and weight so animal size and weight calculator can convert the information into parameters for adjustment of size, distortion, and location of the segmentation template; (e) an animal spine position calculator automatically identifies animal spine and convert into parameters by direction and position of animal spine for adjustment of size, distortion, and location of the segmentation template; and (f) a texture analyzer automatically defines a series of VOI similar to VOI of said predefined segmentation template and generates parameters for adjustment of size, distortion, and location of the segmentation template.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1A illustrates a mouse coronal view;

DESCRIPTION OF THE EXEMPLARY EMBODIMENTS

To further understand and recognize the fulfilled functions and structural characteristics of the disclosure, several exemplary embodiments cooperating with detailed description are presented as follows.

Figure 1:
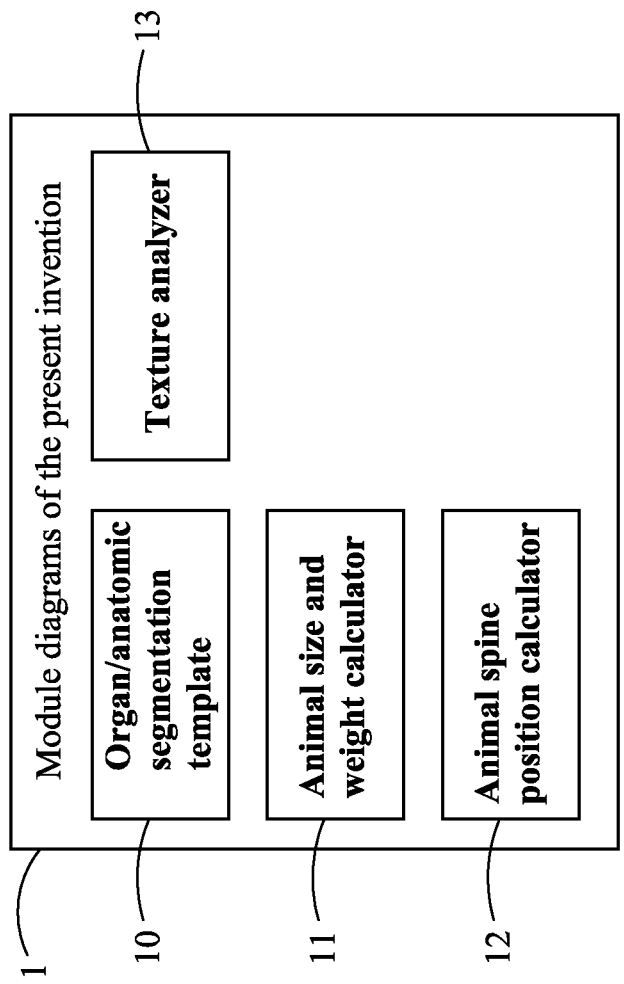
FIG. 1 is module diagram schematically illustrating an embodiment of the present invention.

The present invention can be explained and understood by the following embodiments with corresponding figures. Referring now to FIG. 1, which illustrates a block diagram of VOI System for use with Molecular Imaging Quantization.

The system comprises an organ/anatomic segmentation template 10, an animal size and weight calculator 11, an animal spine position calculator 12, and a texture analyzer 13. Referring to FIG. 1A, the image region 101 is a mouse coronal view. The image region 101 correspond to portions of a CT image. The region 102 contains a set of irregular shapes and are so called organ/anatomic segmentation template 10 when it applies to the image region 101 it forms the image region 111. The organ/anatomic segmentation template 10 contains one or more VOI segmentation areas those are connected slices of irregular shapes. The organ/anatomic segmentation template 10 also contains the record of sizes, positions, and textures of the segmentation areas.

The animal size and weight calculator 11 is used for input of animal size and weight and converts into parameters for conversion of predefined segmentation template 10 to an image of animal being segmented by the ratio of size and weight between animal used to generate predefined template and animal of target image. Referring to FIG. 1A, the region 102 is a predefined template and was created by a rat image. With animal size and weight calculator 11 the present system converts the coordinate space of template into assigned image region 101 and resulted image region 111. The animal size and weight calculator 11 converts coordinate space of template and assigned image so that size, distortion, and location of two coordinate space can be co-registered.

Figure 1B:
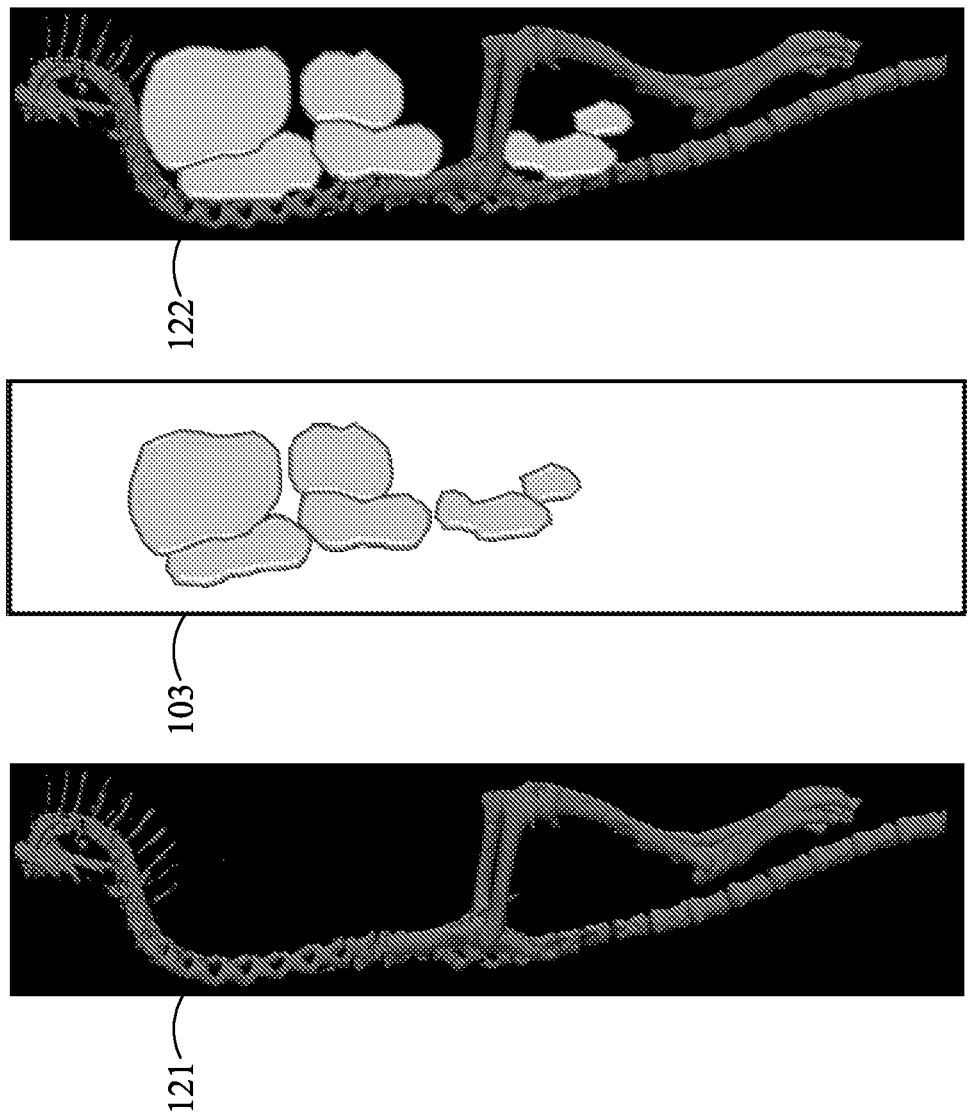
FIG. 1B illustrates an image region of a mouse bone skeleton correspond to portions of a CT image made by setting the threshold of pixels with HU more than 1000.
Figure 1C:
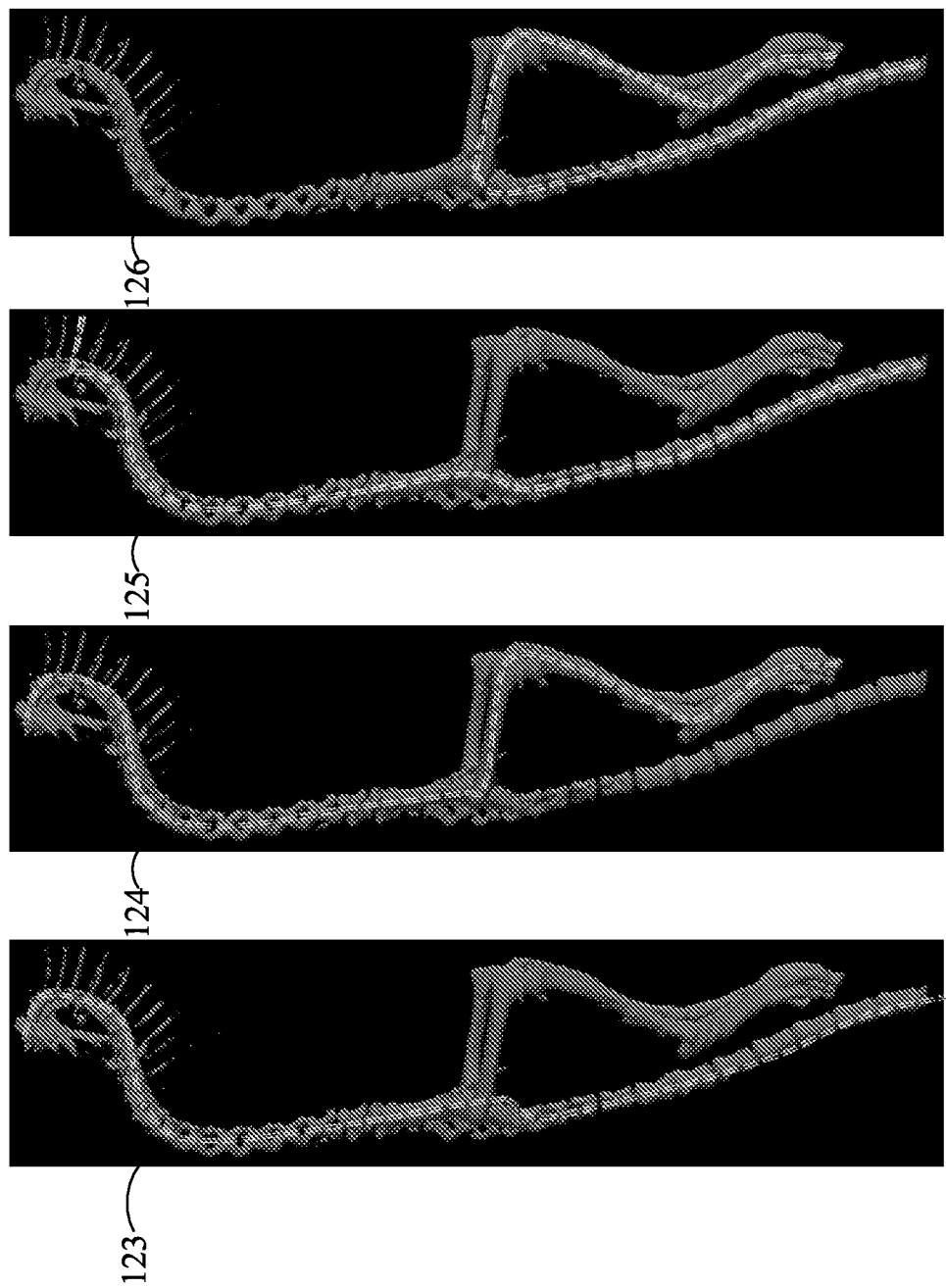
FIG. 1C illustrates the animal spine position calculator for identifying the longest bone path by comparing all the possible paths.

The animal spine position calculator 12 is used to define animal spine direction and detailed position for conversion of parameters for adjustment of size and shape of the segmentation template 10. The animal spine position calculator 12 comprises means for applying the organ/anatomic segmentation template to an image of animal being segmented to determine template placement details. Hounsfield Unit (HU) 1000 is used to identify bones from CT image. Referring to FIG. 1B, the image region 121 is a mouse bone skeleton correspond to portions of a CT image made by setting the threshold of pixels with HU more than 1000. Referring to FIG. 1C, the animal spine position calculator 12 identifies the longest bone path by comparing all the possible paths for example the dashed double lines of 123, 124, 125, and 126. Referring to FIG. 1B, then the predefined template 103 is resized, reshaped and relocated to the found spine path as shown in 122.

Figure 1D:
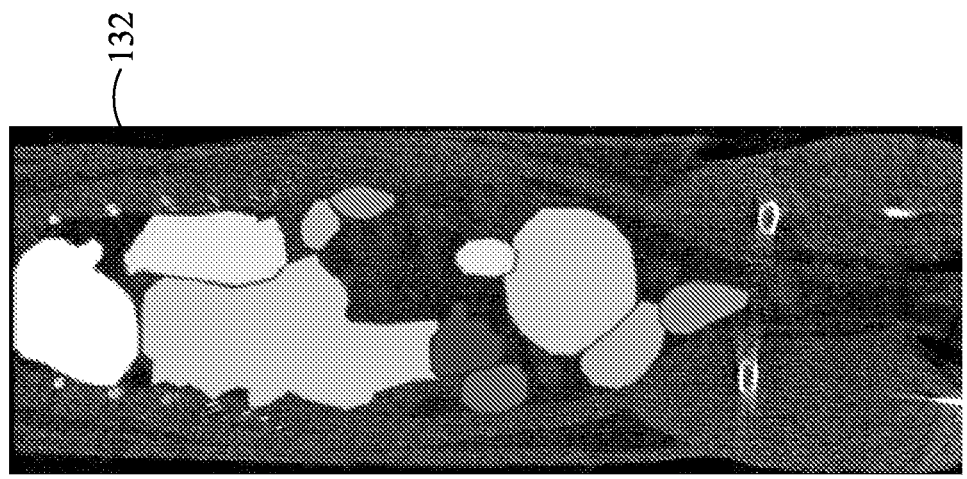
FIG. 1D illustrates a predefined template that is not perfectly match organs of the image region.
Figure 1D:
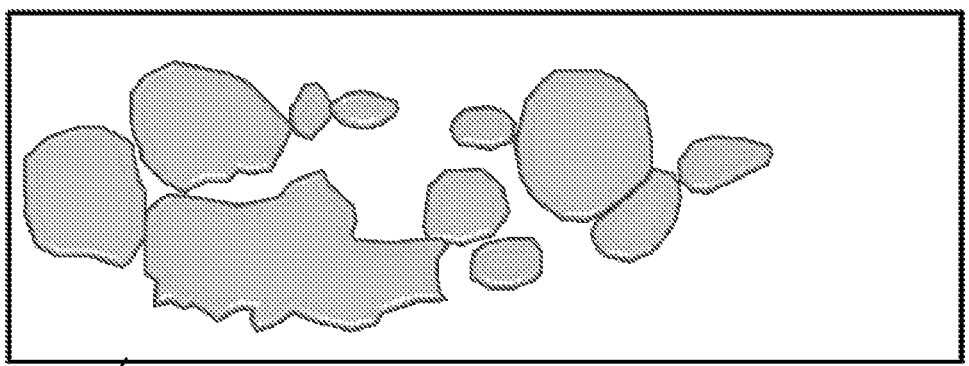
Figure 1D:

The texture analyzer 13 is used to define a series of segmentations with similar texture pattern from CT image for further match of template with image for adjustment of size, shape and location of the segmentation template 10. The texture analyzer comprises means for searching for one or more organ/anatomic regions of the image by matching region textures to a top level configuration. Referring to FIG. 1D, the predefined template 104 is not perfectly match organs of the image region 131. The texture analyzer 13 averages HU of each segmentation areas of template 104 and resize, reshape, and relocate each segmentation area to the image region 131 within a threshold of 10% of the size, shape and location. The resulted image region with template is shown in 132.

Figure 2:
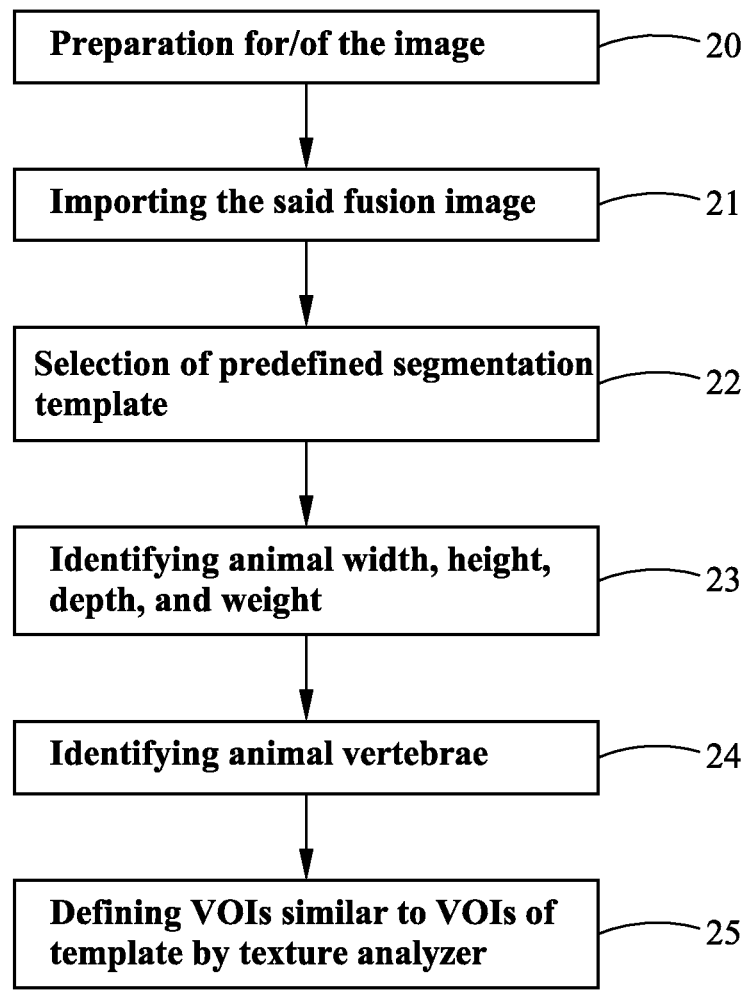
FIG. 2 illustrates the steps for VOI segmentation system for use with molecular imaging quantization.

FIG. 2 illustrates a series of flow diagrams showing the processing performed for VOI segmentation system for use with molecular imaging quantization.

As shown in step 20 of the flow diagrams, preparation for the animal, imaging of the animal, fusion of different modalities, and contract adjustment for the image is done by imaging modality.

As shown in step 21, the co-registered (after fusion) image completed by imaging modality is imported to the system 1 shown in FIG. 1.

As shown in step 22, selection of predefined segmentation template 10 based on study target, animal species, organ and anatomic target of interests is made. For example, a therapeutic efficacy and SPECT/CT imaging study of radiopharmaceutical in colon carcinoma solid tumor model requires a template of organs comprise liver, spleen, kidney, bladder, and the tumor (at the leg). Predefined segmentation is provided for most common species comprise mice, rat, rabbits and human with major organs comprise testis, pancreas, stomach, intestine, kidney, spleen, liver, lung, heart, brain, and tumor (back legs).

As shown in step 23, input of animal width, height, depth, and weight is done so animal size and weight calculator 11 can convert the information into parameters for adjustment of size, distortion, and location of the segmentation template 10.

As shown in step 24, an animal spine position calculator 12 automatically identifies animal spine and convert into parameters by direction and position of animal spine for adjustment of size, distortion, and location of the segmentation template 10.

As shown in step 25, a texture analyzer 13 automatically defines a series of VOI similar to VOI of said predefined segmentation template and generates parameters for adjustment of size, distortion, and location of the segmentation template.

Figure 3:
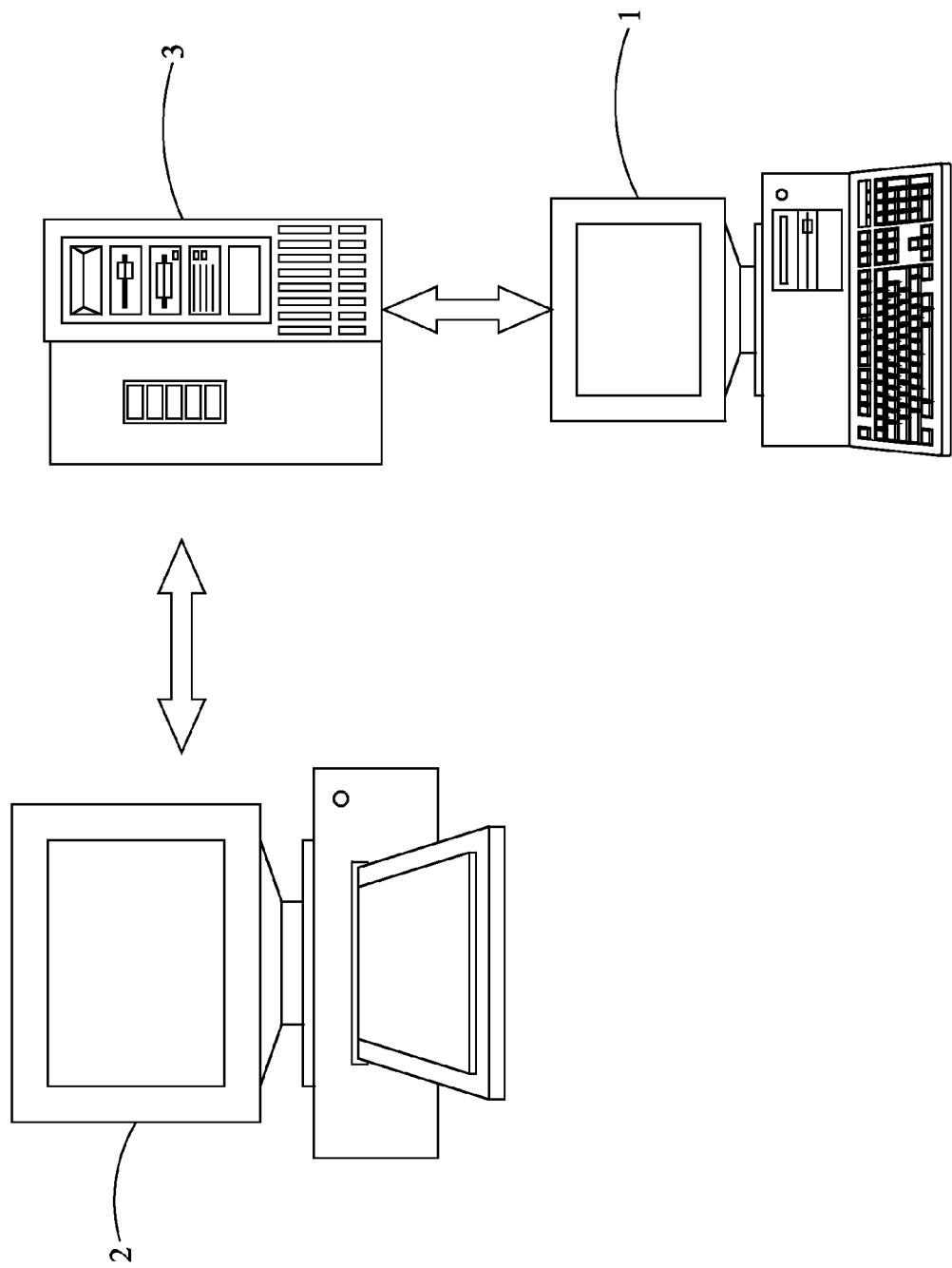
FIG. 3 is a block diagram of an image quantization system.

Referring to FIG. 3, an image quantization system for performing image segmentation includes a VOI segmentation system 1, an imaging modality workstation 2, and an image database 3. The imaging modality workstation 2 uploads the co-registered image to image database 3. VOI segmentation system 1 acquires images through standard protocol such as Digital Imaging and Communications in Medicine (DICOM) or interface file from image database 3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of using a Volume-of-interest (VOI) Segmentation System for use with Molecular Imaging Quantization comprising the steps of:
   (a) preparing an image of a target animal by adjusting fusion of different modalities and contract adjustment;
   (b) importing the image into said VOI Segmentation System comprising an organ/anatomic segmentation template, an animal size and weight calculator, an animal spine position calculator, and a texture analyzer, wherein said organ/anatomic segmentation template is based on study target, animal species, organ, and anatomic target of interests;
   (c) converting animal width, height, depth, and weight into parameters for adjustment of size, distortion, and location of said organ/anatomic segmentation template by said animal size and weight calculator;
   (d) defining animal bone skeleton and identifying spine direction and detailed position by for adjustment of size, distortion, and location of said organ/anatomic segmentation template by said animal spine position calculator; and (e) defining similarities between VOI of said image and VOI of said organ/anatomic segmentation template and generating parameters for adjustment of size, distortion, and location of said organ/anatomic segmentation template by a texture analyzer.

2. The method of claim 1 wherein said organ/anatomic segmentation template comprises: a set of textured regions.

3. The method of claim 1 wherein said animal size and weight calculator comprises means for size, distortion, and location conversion of said organ/anatomic segmentation template to the image being segmented by a size ratio and a weight ratio between a template animal and said target animal.

4. The method of claim 1 wherein said animal spine position calculator comprises means for determining a template placement details by applying the organ/anatomic segmentation template to the image of said target animal.

5. The method of claim 1 wherein said texture analyzer comprises means for searching for one or more organ/anatomic regions of the image by matching region textures to a top level configuration.

* * * * *